United States Patent [19]

Braid

[11] 4,187,186
[45] Feb. 5, 1980

[54] LUBRICANT COMPOSITIONS CONTAINING ESTERS OF BENZOTRIAZOLECARBOXYLIC ACID

[75] Inventor: Milton Braid, Westmont, N.J.

[73] Assignee: Mobil Oil Corporation, New York, N.Y.

[21] Appl. No.: 895,677

[22] Filed: Apr. 12, 1978

[51] Int. Cl.² .............................................. C10M 1/32
[52] U.S. Cl. .......................... 252/51.5 R; 252/51.5 A; 252/49.6; 548/261
[58] Field of Search .............. 260/308 B; 252/51.5 A, 252/51.5 R

[56] References Cited
U.S. PATENT DOCUMENTS

| | | | |
|---|---|---|---|
| 2,943,017 | 6/1960 | Sasse et al. | 424/269 |
| 3,227,726 | 1/1966 | Levy | 260/308 B |
| 3,413,227 | 11/1968 | Howard et al. | 252/51.5 R |
| 3,772,273 | 11/1973 | Gilbert | 424/269 |
| 3,849,433 | 11/1974 | Butula | 260/308 B |
| 3,884,932 | 5/1975 | Andress | 260/308 B |
| 4,014,894 | 3/1977 | Andress | 260/308 B |

*Primary Examiner*—Paul M. Coughlan, Jr.
*Attorney, Agent, or Firm*—Charles A. Huggett; Raymond W. Barclay; Thomas S. Szatkowski

[57] ABSTRACT

Lubricant compositions containing oleagineous materials and, in amounts sufficient to impart thereto resistance to oxidation, wear and metal corrosion, esters of alkylbenzotriazolecarboxylic acid having the formula:

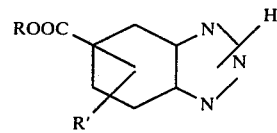

where R is selected from the group consisting of alkyl containing from 1 to about 12 carbon atoms, aralkyl containing from 7 to about 12 carbon atoms and cycloalkyl and alkyl-substituted cycloalkyl containing from about 5 to about 12 carbon atoms; and R' is hydrogen or an alkyl group containing from 1 to about 8 carbon atoms.

7 Claims, No Drawings

LUBRICANT COMPOSITIONS CONTAINING ESTERS OF BENZOTRIAZOLECARBOXYLIC ACID

BACKGROUND OF THE INVENTION

1. Field of the Invention

The invention relates to oleagineous compositions which exhibit antiwear, antioxidant and metal corrosion inhibition properties. In particular, the invention relates to compositions such as mineral and synthetic lubricating oils, gear oils, transmission fluids, greases, and other oleagineous compositions normally requiring the presence of antiwear, antioxidant or anticorrosion additives.

2. Description of the Prior Art

Prior to the present invention, triazole materials have been employed in lubricant compositions as metal deactivators. For example, U.S. Pat. No. 3,597,353 of Randell et al. discloses the use of 4, 5, 6, 7-tetrahydrobenzotriazole as a metal deactivating additive for natural and synthetic lubricants. Similarly, U.S. Pat. No. 3,413,227 of Howard et al. teaches that an alkyl-substituted benzotriazole where the alkyl group contains from 2 to 20 carbon atoms can be used as a corrosion or tarnish inhibitor.

In U.S. Pat. No. 4,060,491, Bridger et al. teach utilizing 5-alkylbenzotriazoles, in which the alkyl group contains from 4 to 16 carbon atoms, in a method for reducing wear between moving steel-on-steel surfaces.

In U.S. Pat. No. 3,788,993 of Andress, it is taught that benzotriazoles react with alkyl or alkenylsuccinic anhydrides to form reaction products which impart corrosion inhibiting properties to lubricating oils.

Nnadi et al., in U.S. Pat. No. 4,048,082, disclose that esters of adducts of benzotriazole and unsaturated dicarboxylic acids or anhydrides thereof impart antirust properties to organic compositions.

None of the prior art patents disclose the esters of alkylbenzotriazolecarboxylic acid of the present invention.

SUMMARY OF THE INVENTION

It has now been found that esters of alkylbenzotriazolecarboxylic acid, having the formula:

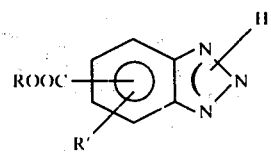

where R is selected from the group consisting of alkyl containing from 1 to about 12 carbon atoms, aralkyl containing from 7 to about 12 carbon atoms, cycloalkyl and alkyl-substituted cycloalkyl containing from about 5 to about 12 carbon atoms; and R' is hydrogen or an alkyl group containing from 1 to about 8 carbon atoms, impart antiwear, antioxidant and metal corrosion inhibition properties to the lubricant compositions to which they are added.

Referring to the above formula, when R is alkyl, the group can be of any isomeric arrangement. Exemplary are alkyl groups such as methyl, ethyl, butyl, isobutyl, octyl, 2,2,4-trimethylpentyl, dodecyl, 2,4,4-triethylpentyl and 2-ethyl hexyl.

Exemplary of the aralkyl groups which can constitute the R substituent in the above formula are benzyl, phenethyl, and 3-phenylpropyl.

Exemplary of the cycloalkyl and alkyl-substituted cycloalkyl groups which can constitute the R substituent in the above formula are cyclopentyl, methyl cyclopentyl, cyclohexyl, hexylcyclohexyl and the like.

Preferred are those esters having the formula:

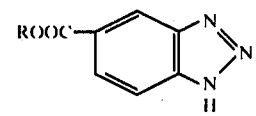

where R is an alkyl group containing from 1 to about 12 carbon atoms. Particularly preferred is where R is an alkyl group containing from 2 to about 10 carbon atoms. Most particularly preferred is where R is an alkyl group containing from about 2 to about 8 carbon atoms.

Of particular significance, in accordance with the present invention, is the ability to improve the antiwear, antioxidant and metal corrosion resistance of oleagineous materials such as lubricating media which may comprise liquid hydrocarbon oils in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-dethyl hexyl) sebacate, di(2-ethyl hexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers.

It is to be understood, however, that the compositions contemplated herein can also contain other materials. For example, antirust agents, extreme pressure agents, viscosity index agents, supplementary or co-antioxidants and the like can be used. These materials do not detract from the value of the compositions of this invention, rather these materials serve to impart their customary properties to the particular compositions in which they are incorporated.

Also contemplated in accordance with the present invention are the mineral oil heat exchange fluids which have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions." Specifications for low-temperature and aircraft fluids are defined in U.S. Government Specification MIL-H-5606A.

Also, functional fluids such as hydraulic fluids and metal working fluids can be utilized in the compositions of the present invention.

In general, the esters of alkylbenzotriazolecarboxylic of the present invention may be employed in any amount which is effective for imparting the desired degree of antiwear improvement, antioxidant characteristics or metal corrosion prevention. In many applications, however, the additive is effectively employed in amounts from about 0.01 to about 10% by weight, and preferably from about 0.1 to about 5% of the total weight of the composition.

The novel esters of benzotriazolecarboxylic acids are produced either by ring closure via diazotization of a 3,4-diaminobenzoic acid followed by esterification:

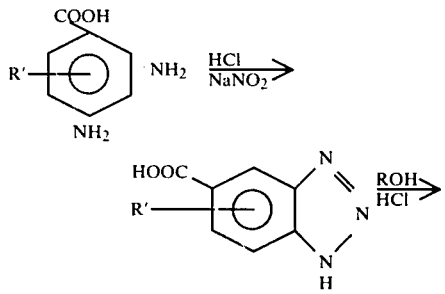

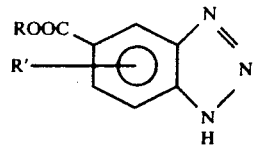

or by esterification of the diaminoalkylbenzoic acid followed by ring closure:

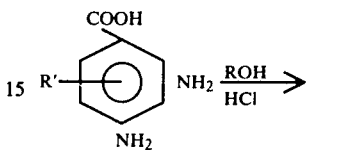

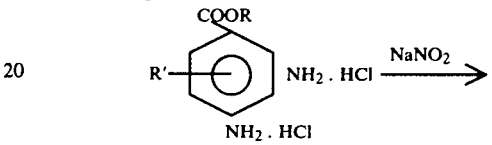

It has been found that the diaminobenzoic acids and the benzotriazolecarboxylic acids can be effectively esterified via reaction with the desired alcohol which has been saturated with anhydrous hydrogen chloride using procedures well known in the art.

A large molar excess of the alcohol to the carboxylic acid is employed, ranging from about 2:1 to about 30:1. The reaction will proceed at temperatures from about 60° C. to about 200° C. with from about 65° C. to about 150° C. being preferred when no solvent is used. The reaction may be conducted with refluxing and removal of water by azeotroping when the alcohol used is not water soluble. The reaction may be carried out at reduced pressure to avoid consumption of the alcohol in the formation of contaminating ethers. Reaction times generally range from 2 to about 20 hours.

Alternatively a solvent such as benzene, toluene, or xylene may be employed and water may be removed by azeotropic distillation.

The ring closure reaction for 3,4-diaminoalkylbenzoic acid and ethyl 3,4-diaminoalkylbenzoate is known to the art. In general, the diamino compounds are contacted with nitrous acid formed from NaNO₂, and a mineral acid such as hydrochloric acid at temperatures of from about 0° C. to about 5° C. for about 1 to about 4 hours.

DESCRIPTION OF SPECIFIC EMBODIMENTS

The following examples and comparative data will serve to illustrate the novel esters of alkylbenzotriazolecarboxylic acid of the present invention, and the marked improvement in antioxidant, antiwear and copper corrosion inhibition properties of oleagineous materials containing those esters. It will be understood, however, that it is not intended that the invention be limited to the particular compositions containing those esters described herein. Various modifications of those esters and compositions can be employed, as will be readily apparent to those skilled in the art.

EXAMPLE 1

Preparation of ethyl benzotriazolecarboxylate via ring closure followed by esterification. To 75 gms of 3,4-diaminobenzoic acid in 2400 ml of water were added 75 gms of concentrated hydrochloric acid at 20°-30° C. The reaction mixture was cooled to 5° C. while an additional 1400 ml of water was added. A solution of 27.5 gms of sodium nitrite in 325 ml of water was added while stirring at 5° C. during 1.5 hr. The mixture was allowed to warm to room temperature during about 2 hr. The reaction product which precipitated during this period was collected on a filter and recrystallized from ethanol. Benzotriazolecarboxylic acid, having an empirical formula $C_7H_5O_2N_3$, was obtained as a crystalline solid having a melting point of 298° C. with decomposition. The elemental analysis, wt %, was as follows:

|  | C | H | N |
|---|---|---|---|
| Calculated for $C_7H_5O_2N_3$ | 51.54 | 3.09 | 25.76 |
| Found | 50.98 | 3.17 | 25.0 |

Esterification of the acid so obtained was carried out by passing gaseous hydrogen chloride into 100 ml of ethanol to saturation. To the saturated ethanol 6.3 g of benzotriazole carboxylic acid was added, and the mixture was heated at reflux for 7.75 hr. The reaction mixture was poured into water and the solids precipitated thus, and by neutralization with sodium bicarbonate were collected, m.p. 110°-111° C. The infrared spectrum and non-depression of melting point upon admixture with the same ester obtained by an alternate synthesis route in Example 2 confirmed that the solid was ethyl benzotriazole carboxylate.

EXAMPLE 2

Preparation of ethyl benzotriazolecarboxylate via esterification followed by ring closure.

Ethanol (100 ml) was saturated with hydrogen chloride and 15 g of 3,4-diaminobenzoic acid was added. The reaction mixture was refluxed for a total of 19 hrs. The reaction mixture was cooled, the solids were collected by filtration, washed with ammonium hydroxide solution, dried, and recrystallized from benzene.

Ethyl 3,4-diaminobenzoate having an empirical formula $C_9H_{12}O_2N_2$, was obtained as a crystalline solid having an mp 109°-110° C. The elemental analysis was as follows:

|  | C | H | N |
|---|---|---|---|
| Calculated for $C_9H_{12}O_2N_2$ | 55.99 | 6.71 | 15.55 |
| Found | 53.93 | 6.77 | 15.9 |

The nmr and infrared spectra indicated the solid to have the following structure:

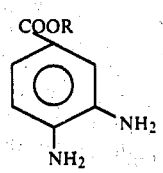

Ring closure of this solid was carried out by adding 6 g of ethyl 3,4-diaminobenzoate to a mixture of 150 ml of water, 100 g of ice, and 10.5 g of concentrated hydrochloric acid. To the resulting clear solution there was added during 2.25 hr. while stirring at 0°-5° C., a solution of 2.9 g of sodium nitrite in 125 ml of water. The reaction mixture was stirred at about 5° C. for an additional 0.5 hr. and then filtered. The solids collected thus were washed with dilute aqueous sodium bicarbonate solution then with water and air dried. The solids were recrystallized from benzene.

Ethyl benzotriazolecarboxylate was obtained as a crystalline solid, mp 112°-113° C. The 1H nmr $(CDCl_3)\delta 14$ ppm (broad, NH), 9.7 (d, H-4), 8.1 (d of d, H-6) 7.9 (d, H-7), 4.4 (q, $CH_2$), 1.4 (t, $CH_3$) and infrared spectra indicated the structure to be as follows:

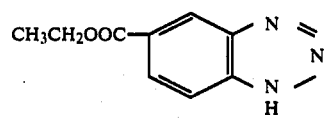

The elemental analysis was as follows:

|  | C | H | N |
|---|---|---|---|
| Calculated for $C_9H_9O_2N_3$ | 56.54 | 4.74 | 21.98 |
| Found | 56.34 | 4.76 | 22.2 |

EXAMPLE 3 n-Octyl alcohol (300 g) was saturated with hydrogen chloride gas passed in subsurface during about 2 hr. while the temperature rose to 55° C. Benzotriazolecarboxylic acid (16.3 g) prepared by the method of Example 1 was added and the reaction mixture was refluxed at 110° C. under reduced pressure for 1.25 hr. during which water was azeotropically distilled and collected in a Dean-Stark trap. Unreacted octyl alcohol was removed by reduced pressure distillation. The residue, which was solid when cooled, was recrystallized from benzene and washed with n-pentane to afford the ester, n-octyl benzotriazolecarboxylate, as a solid mp 64°-65° C. The infrared spectrum was similar to that of the ethyl ester, consistent with the ester structure, and the elemental analysis was as follows:

|  | C | H | N |
|---|---|---|---|
| Calculated for $C_{15}H_{21}O_2N_3$ | 65.43 | 7.69 | 15.26 |
| Found | 64.87 | 7.61 | 14.9 |

The esters of benzotriazolecarboxylate produced in the above examples were then tested for antiwear, oxidation inhibition and copper corrosion prevention activity.

For the oxidation test, the esters were blended into a neutral solvent refined mineral base oil having a viscosity at 100° F. of 130 SUS. The oils were then subjected to a stream of air at the rate of 10 liters per hour at a temperature of 325° F. for 40 hours in the presence of metals having pro-oxidant properties: iron, copper, lead and aluminum. The lead sample was weighed before and after the test, since lead is one of the metals more susceptible to corrosion by oxidation. The test measurements are change in acidity or neutralization number (ΔNN) as measured by ASTM D-974, change in kinematic viscosity at 210° F. (ΔKV), lead loss in milligrams, and sludge. Results of the test are presented in Table 1.

TABLE I

Catalytic Oxidation Test, Mineral Oil, 325° F. 40 hrs.

| Base Oil | Δ NN | Δ KV | Pb Loss, mg | Sludge |
|---|---|---|---|---|
| Base oil without additive Ester of Example 3 | 17 | 334 | 66 | Heavy |
| Base oil + 1 wt % ester | 4.86 | 33 | 4.7 | Heavy |

The oxidation test was repeated but with a base oil consisting of a synthetic ester lubricant which is prepared by esterification of technical grade pentaerythritol with a mixture of commercial monocarboxylic (valeric and pelargonic) acids at a temperature of 450° F. for 24 hours. The results are presented in Table 2.

TABLE 2

Catalytic Oxidation Test, Synthetic Ester, 450° F., 24 hrs.

| Base Oil | Δ NN | Δ KV | Pb Loss, mg | Sludge |
|---|---|---|---|---|
| Base oil without additive Ester of Example 3 | 8.25 | 586 | 13.7 | Trace |
| Base oil + 2 wt % ester | 2.93 | 433 | 1.3 | Light |
| Base oil + 1 wt % ester | 4.26 | 602 | 2 | Light |

As shown by the data presented in Tables 1 and 2, the oxidative stability of the base oil is markedly improved by the addition of the esters of the present invention.

The esters were then tested for antiwear properties using the Shell Four Ball Wear Test. In general, three steel balls of SAE 52-100 steel are held in a ball cup. A fourth ball, positioned on a rotatable vertical axis is brought into contact with the three balls and is rotated against them. The force which the fourth ball is held against the three stationary balls may be varied according to a desired load. The test lubricant is added to the ball cup and acts as a lubricant for the rotation. At the end of the test the steel balls are investigated for wear scar; the extent of scarring represents the effectiveness of the lubricant as an antiwear agent. The esters of the present invention, at a concentration of 0.1 wt %, were tested in a solvent refined mineral lubricating oil having a 239.1 SSU viscosity at 100° F. and a 475° F. minimum flash point. The test conditions were 40 Kg load, 600 RPM, 30 minutes test time and temperatures of 200° F. and 400° F. The results are reported in Table 3 as wear scar diameter and as wear rate, volume of wear per unit sliding distance per kilogram of load.

TABLE 3

| Additive | Antiwear Test Test Temp. °F. | Wear Scar Diameter, mm | Wear rate × $10^{12}$ cc/cm-kg |
|---|---|---|---|
| None | 200 | 0.6858 | 4.6 |
| " | 400 | 0.8341 | 10.5 |
| Ester of Example 2 | 200 | 0.3556 | 0.15 |
| Ester of Example 2 | 400 | 0.4013 | 0.35 |

The data of Table 3 shows the improved antiwear properties imparted to the base lubricant by the esters of the present invention.

The esters of this invention were tested for anticorrosion properties in the ASTM D130 Test. The base oil was Arabian Light stock which was made corrosive by the addition of 40 ppm elemental sulfur. The ester was blended into the base oil at a concentration of 0.1 wt. %.

In general, the ASTM D130 Test involves immersing a polished copper strip in the oil blend and heating at 212° F. for 6 hours. At the end of this period the strip was removed, washed, and compared with ASTM Copper Strip Corrosion Standards. The results are presented in Table 4.

TABLE 4

| ASTM D-130 Copper Corrosion Test | Rating |
|---|---|
| Base oil (includes 40 ppm sulfur) | 4B |
| Base oil + .1 wt % ester of Example 2 | 2A |

A rating of 1A or 1B denotes a slight tarnish, a rating of 2A, 2B, 2C, 2D and 2E denotes a moderate tarnish; a rating of 3A or 3B denotes a dark tarnish and a rating of 4A, 4B, or 4C denotes severe corrosion.

The results presented in Table 4 indicate the efficacy of the esters of the present invention in reducing copper corrosion.

I claim:

1. A lubricant composition which comprises an oleagineous material, and, in an amount effective to impart antiwear, antioxidant and copper corrosion prevention properties thereto, an ester of benzotriazolecarboxylic acid having the formula;

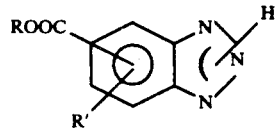

where R is selected from the group consisting of alkyl containing from 1 to 12 carbon atoms, aralkyl containing from 7 to 12 carbon atoms and cycloalkyl and alkyl-substituted cycloalkyl containing from 5 to about 12 carbon atoms; and R' is hydrogen or an alkyl group containing from 1 to 8 carbon atoms.

2. The composition of claim 1 wherein said oleagineous material is selected from the group consisting of mineral oils, synthetic oils and greases thereof.

3. The composition of claim 1 wherein said ester is present in an amount from about 0.01 to about 10% by weight of the total composition.

4. The composition of claim 1 wherein said ester is present in an amount from about 0.1 to about 5% by weight of the total composition.

5. The composition of claim 1 wherein R is an alkyl group containing from 1 to 12 carbon atoms, and R' is hydrogen.

6. The composition of claim 1 wherein said ester is ethyl benzotriazolecarboxylate having the formula:

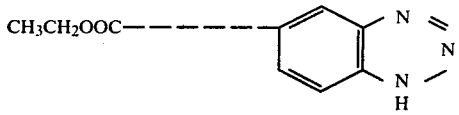

7. The composition of claim 1 wherein said ester is n-octyl benzotriazolecarboxylate having the formula:

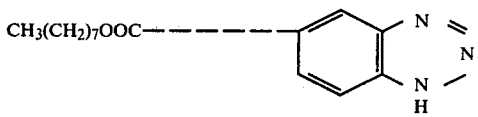

* * * * *